US010692346B2

(12) United States Patent
Carr et al.

(10) Patent No.: US 10,692,346 B2
(45) Date of Patent: Jun. 23, 2020

(54) ELECTRONIC FALL MONITORING SYSTEM

(71) Applicant: TIDI Products, LLC, Neenah, WI (US)

(72) Inventors: Roy Seizo Carr, Fontana, CA (US); Glen Holt Humphrey, North Hills, CA (US); Drew Deem Coatney, Chicago, IL (US); Himanshu Patel, Rancho Santa Margarita, CA (US); Lisa McHale, Lafayette, CO (US)

(73) Assignee: TIDI Products, LLC, Neenah, WI (US)

( * ) Notice: Subject to any disclaimer, the term of this patent is extended or adjusted under 35 U.S.C. 154(b) by 0 days.

(21) Appl. No.: 16/423,348

(22) Filed: May 28, 2019

(65) Prior Publication Data

US 2020/0126389 A1 Apr. 23, 2020

Related U.S. Application Data

(60) Provisional application No. 62/748,886, filed on Oct. 22, 2018.

(51) Int. Cl.
*G08B 23/00* (2006.01)
*G08B 21/04* (2006.01)
(Continued)

(52) U.S. Cl.
CPC ........ *G08B 21/0446* (2013.01); *A61B 5/1115* (2013.01); *A61B 5/1117* (2013.01);
(Continued)

(58) Field of Classification Search
CPC .... G08B 21/0446; G16H 40/00; G16H 40/63; G16H 10/60; G16H 40/20; G06F 3/0482; G06F 15/00
See application file for complete search history.

(56) References Cited

U.S. PATENT DOCUMENTS

| 4,907,845 A | 3/1990 | Wood |
| 5,554,835 A | 9/1996 | Newham |

(Continued)

OTHER PUBLICATIONS

"Sitter Elite Instruction Manual", manual, 2015, 40 pages, Posey Company, Arcadia, California.
(Continued)

*Primary Examiner* — Toan N Pham
(74) *Attorney, Agent, or Firm* — Boyle Fredrickson, S.C.

(57) ABSTRACT

The present invention provides an improved electronic fall monitoring system comprising a device having multiple sensor ports for flexibly monitoring various sensors associated with a single patient without requiring repeated connections and disconnections of sensors. With several sensors simultaneously connected at different locations, a processor can execute to ensure that only one sensor, corresponding to one patient, is monitored at any given time, including by triggering an alarm when a second sensor is triggered while a first sensor is in use. In addition, operation of the device can be simplified with a single multi-color LED illuminating in different colors corresponding to different states of the system. Also, a power switch for turning the device on or off, such as for conserving power, can be placed in a recess of the device so that it is blocked when mounted, thereby avoiding being turned off when it should be monitoring.

20 Claims, 15 Drawing Sheets

(51) Int. Cl.
*A61B 5/11* (2006.01)
*A61B 5/00* (2006.01)

(52) U.S. Cl.
CPC ............ *A61B 5/7405* (2013.01); *A61B 5/746* (2013.01); *A61B 5/7445* (2013.01)

(56) References Cited

U.S. PATENT DOCUMENTS

| | | |
|---|---|---|
| 5,751,214 A | 5/1998 | Cowley et al. |
| 5,844,488 A | 12/1998 | Musick |
| 6,078,261 A | 6/2000 | Daysko |
| 6,111,509 A | 8/2000 | Holmes |
| 6,166,644 A * | 12/2000 | Stroda ................... A61B 5/1113 340/521 |
| 6,441,742 B1 | 8/2002 | Lovely et al. |
| 6,727,445 B2 | 4/2004 | Cullinan et al. |
| 6,784,797 B2 | 8/2004 | Smith et al. |
| 6,847,301 B1 | 1/2005 | Olson |
| 6,897,781 B2 | 5/2005 | Cooper et al. |
| 6,987,232 B2 | 1/2006 | Smith et al. |
| 6,998,986 B2 | 2/2006 | Smith |
| 7,078,676 B2 | 7/2006 | Smith et al. |
| 7,079,036 B2 | 7/2006 | Cooper et al. |
| 7,253,366 B2 | 8/2007 | Bhai |
| 7,319,400 B2 | 1/2008 | Smith et al. |
| 7,378,975 B1 | 5/2008 | Smith et al. |
| 7,557,719 B1 | 7/2009 | Long |
| 7,568,246 B2 | 8/2009 | Weismiller et al. |
| 7,570,152 B2 | 8/2009 | Smith et al. |
| 7,656,299 B2 | 2/2010 | Gentry et al. |
| 7,666,151 B2 | 2/2010 | Sullivan et al. |
| 7,746,218 B2 | 6/2010 | Collins, Jr. et al. |
| 7,883,480 B2 | 2/2011 | Dunlop |
| 7,916,036 B1 * | 3/2011 | Pope ....................... G08B 21/02 200/85 A |
| 8,085,154 B2 | 12/2011 | Williams et al. |
| 8,325,053 B2 | 12/2012 | Flynt et al. |
| 8,416,084 B2 | 4/2013 | Beltmann et al. |
| 8,604,917 B2 | 12/2013 | Collins et al. |
| 8,717,181 B2 | 5/2014 | Tallent et al. |
| 8,749,391 B2 | 6/2014 | Flinsenberg et al. |
| 8,752,220 B2 | 6/2014 | Sodeberg et al. |
| 8,866,620 B2 | 10/2014 | Amir |
| 8,911,377 B2 | 12/2014 | Al-Ali |
| 8,933,801 B2 | 1/2015 | Sweeney et al. |
| 8,990,041 B2 | 3/2015 | Grabiner et al. |
| 9,013,313 B2 | 4/2015 | Paine |
| 9,098,993 B2 | 8/2015 | Reed, Jr. |
| 9,153,114 B2 | 10/2015 | Yi et al. |
| 9,202,361 B2 | 12/2015 | Rubio Andres et al. |
| 9,275,533 B2 | 3/2016 | Sullivan et al. |
| 9,411,934 B2 | 8/2016 | Robinson et al. |
| 9,466,204 B2 | 10/2016 | Olson |
| 9,495,855 B2 | 11/2016 | Hanson et al. |
| 9,558,641 B2 | 1/2017 | Brasch et al. |
| 9,861,321 B2 | 1/2018 | Collins, Jr. et al. |
| 9,866,797 B2 * | 1/2018 | Clark ............... G08B 13/19652 |
| 10,043,368 B1 | 8/2018 | Fonzi, III et al. |
| 10,098,593 B2 | 10/2018 | Collins, Jr. et al. |
| 2010/0298742 A1 | 11/2010 | Perlman et al. |
| 2012/0095722 A1 | 4/2012 | Ten Kate |
| 2014/0221876 A1 | 8/2014 | Eddy |
| 2014/0232556 A1 | 8/2014 | Williams |
| 2015/0226764 A1 | 8/2015 | Ten Kate |
| 2017/0124844 A1 | 5/2017 | Huster et al. |
| 2017/0236398 A1 | 8/2017 | Eddy et al. |
| 2018/0125413 A1 | 5/2018 | Smith, Jr. et al. |

OTHER PUBLICATIONS

"Fall Management System M200 Fall Monitor", manual, 2016, 44 pages, Stanley Security Solutions, Lincoln, Nebraska.

* cited by examiner

ELECTRONIC FALL MONITORING SYSTEM

CROSS-REFERENCE TO RELATED APPLICATION(S)

This is a non-provisional patent application based upon U.S. provisional patent application Ser. No. 62/748,886, entitled "Electronic Fall Monitoring System," filed Oct. 22, 2018, which is incorporated herein by reference.

FIELD OF THE INVENTION

The present invention relates to the field of patient care, and more particularly, to electronic fall monitoring systems having sensor ports operable to connect to patient sensors for detecting activations indicating physical presence of a patient at a patient sensor and deactivations indicating loss of physical presence of the patient at the patient sensor.

BACKGROUND OF THE INVENTION

Electronic fall monitoring systems are typically used in healthcare facilities to provide an early warning as to when a patient who is at risk for falling is attempting to get up without assistance. Although fall monitoring systems do not themselves prevent falls, they can provide advance notification to others that a patient is moving from the sensor so that assistance can be rendered.

Fall monitoring systems typically include a device connected to a pressure sensitive sensor or mat. When a patient rests on the sensor, which could be placed on a bed or chair, the sensor triggers the device to begin monitoring. When the patient later moves from the sensor, unless the device is suspended or powered down, the device can initiate an alarm. Possible alarms include an audible tone, playback of a recorded statement to return to the sensor and/or a message sent to a nurse call station. While fall monitoring systems are effective for providing early warning when a patient is moving, it is nevertheless desirable to increase their capability, robustness and ease of use where possible.

SUMMARY OF THE INVENTION

The present invention provides an improved electronic fall monitoring system comprising a device having multiple sensor ports for flexibly monitoring various sensors associated with a single patient without requiring repeated connections and disconnections of sensors. With several sensors simultaneously connected at different locations, a processor can execute to ensure that only one sensor, corresponding to one patient, is monitored at any given time, including by triggering an alarm when a second sensor is triggered while a first sensor is in use. In addition, operation of the device can be simplified with a single multi-color LED illuminating in different colors corresponding to different states of the system. Also, a power switch for turning the device on or off, such as for conserving power, can be placed in a recess of the device so that it is blocked when mounted, thereby avoiding being turned off when it should be monitoring.

Specifically then, one aspect of the present invention can provide an electronic fall monitoring system, including: multiple sensor ports, each sensor port being operable to connect to a patient sensor for detecting an activation indicating a physical presence at the patient sensor and a deactivation indicating a loss of physical presence at the patient sensor; a standby input; and a processor executing a program stored in a non-transient medium, the processor executing the program to: select a mode from among multiple modes, the modes including a monitor mode in which a sensor port connected to a patient sensor is monitored for a deactivation, an alarm mode in which an alarm is active following a deactivation detected in the monitor mode, and a standby mode in which the alarm is inactive, in which the standby mode is selected before an activation is detected at any sensor port, the monitor mode is selected when an activation is detected at a first sensor port, the alarm mode is selected when a deactivation is detected at the first sensor port following the activation, and selection of the standby input causes a temporary transition to the standby mode from either the monitor mode or the alarm mode Another aspect of the present invention can provide an electronic fall monitoring system, including: multiple sensor ports, each sensor port being operable to connect to a patient sensor for detecting an activation indicating a physical presence at the patient sensor and a deactivation indicating a loss of physical presence at the patient sensor; a multi-color Light Emitting Diode (LED); and a processor executing a program stored in a non-transient medium, the processor executing the program to: select a mode from among multiple modes, the modes including a monitor mode in which a sensor port connected to a patient sensor is monitored for a deactivation, an alarm mode in which an alarm is active following a deactivation detected in the monitor mode, and a standby mode in which the alarm is inactive, and illuminate the multi-color LED in a given color for indicating a given mode of the plurality of modes.

Another aspect of the present invention can provide an electronic fall monitoring system, including: a housing enclosing electronics including a processor; multiple sensor ports accessible through the housing, each sensor port being operable to connect to a patient sensor for allowing the processor to detect an activation indicating a physical presence at the patient sensor and a deactivation indicating a loss of physical presence at the patient sensor; a power switch accessible through the housing for controlling power to the electronics; and a recess in the housing shaped for mounting the housing to a support mechanism, in which the power switch is disposed in the recess so that the power switch is inaccessible when the housing is mounted to the support mechanism.

These and other objects, advantages and aspects of the invention will become apparent from the following description. The particular objects and advantages described herein can apply to only some embodiments falling within the claims and thus do not define the scope of the invention. In the description, reference is made to the accompanying drawings which form a part hereof, and in which there is shown a preferred embodiment of the invention. Such embodiment does not necessarily represent the full scope of the invention and reference is made, therefore, to the claims herein for interpreting the scope of the invention.

BRIEF DESCRIPTION OF THE DRAWINGS

Preferred exemplary embodiments of the invention are illustrated in the accompanying drawings in which like reference numerals represent like parts throughout, and in which.

DETAILED DESCRIPTION OF THE INVENTION

Referring now to FIGS. 1-4, in accordance with an aspect of the invention, in front, rear and first and second side views, respectively, an electronic fall monitoring system 10 can comprise a device 12 connected to multiple patient sensors (not shown) for providing an early warning as to when a patient who is at risk for falling is attempting to get up without assistance. As shown in the front view of FIG. 1, the device 12 can include a microphone 14, a speaker 16, a multi-color LED 18, also identified by "Status," and a battery level indicator LED 20. The microphone 14 can be used to record a statement which could be played back through the speaker 16, such as a recorded statement played to a patient to return to the sensor when alarming. The speaker 16 can be used to create an alarm, such as an audible tone and/or playback of the recorded statement, and/or can be used to play audible cues, such as instructions for setting up the fall monitoring system 10, instructions for resolving an alarm condition, and the like. The multi-color LED 18 can indicate by color various modes of operation of the fall monitoring system 10, such as illuminating green to indicate a "monitor mode" in which a sensor port connected to a patient sensor is being monitored for a deactivation, illuminating red to indicate an "alarm mode" in which an alarm is active following a deactivation detected in the monitor mode and/or illuminating yellow to indicate a "standby mode" in which the alarm is inactive. The battery level indicator LED 20 can indicate a status or charge of batteries powering the device 12, such as when disconnected from a wired power source, such as by flashing red when the batter is low (for example, below 20% charge). This essentially simplifies readability of the device.

Figure 1:
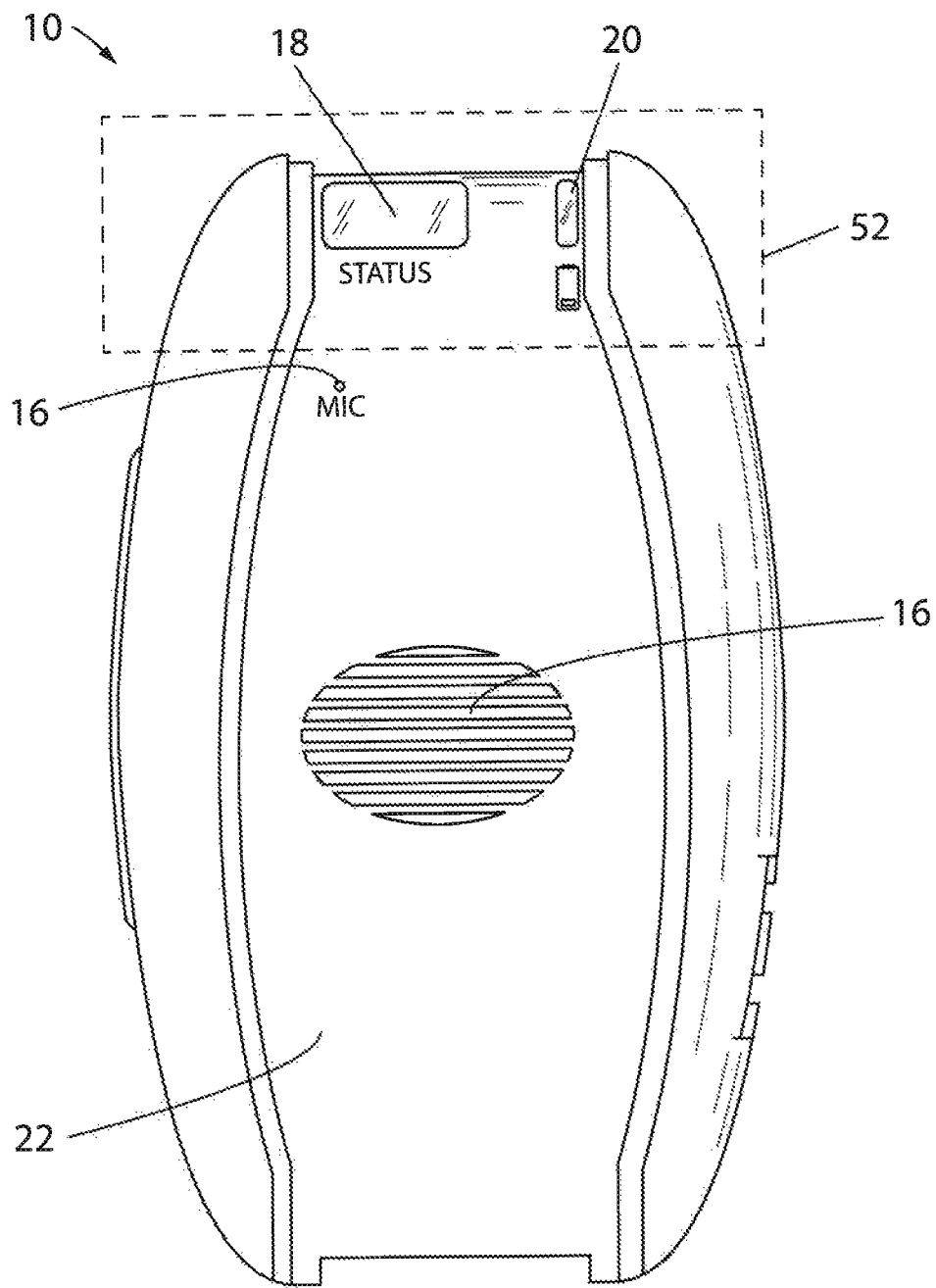
FIG. 1 is a front view of an electronic fall monitoring system in accordance with an aspect of the invention.
Figure 2:
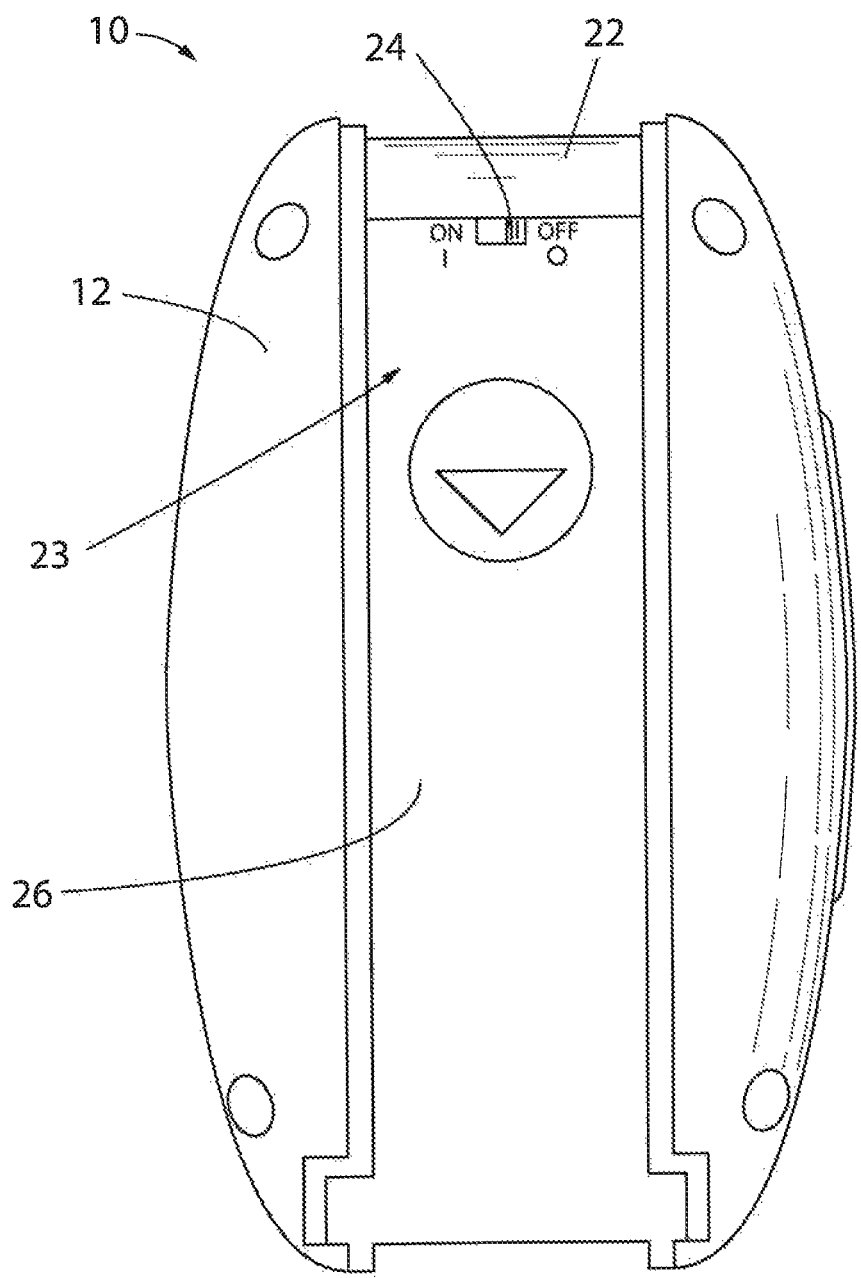
FIG. 2 is a rear view of the electronic fall monitoring system of FIG. 1.

As shown in the rear view of FIG. 2, a back portion of an external housing 22 or enclosure of the device 12 can include a recess 23 for mounting the device 12 to a support mechanism. The support mechanism could be, for example, a bracket, clip, bar or other arrangement held to a structure, such as a wall or chair. A power switch 24 can be accessible through the housing 22 for controlling power to electronics of the device 12, such as a processor, for turning the device 12 on or off. In one aspect, the electronics of the device 12 could be implemented on four-layer circuit board with a plurality of diodes providing electrostatic discharge (ESD) protection with respect to the various ports as described herein. The power switch 24 can be configured to allow actuation by hand, such as a finger sliding a manual electric switch, without requiring a tool. The power switch 24 can be disposed on the back of the device 12, in the recess 23, so that the power switch 24 is completely covered by a support mechanism, and therefore completely inaccessible, when mounted to the support mechanism. A battery cover 26, positioned below the power switch 24, for covering a battery compartment containing batteries for powering the device 12, can also be disposed in the recess 23, so that the batteries are also completely inaccessible when mounted to the support mechanism.

Figure 3:
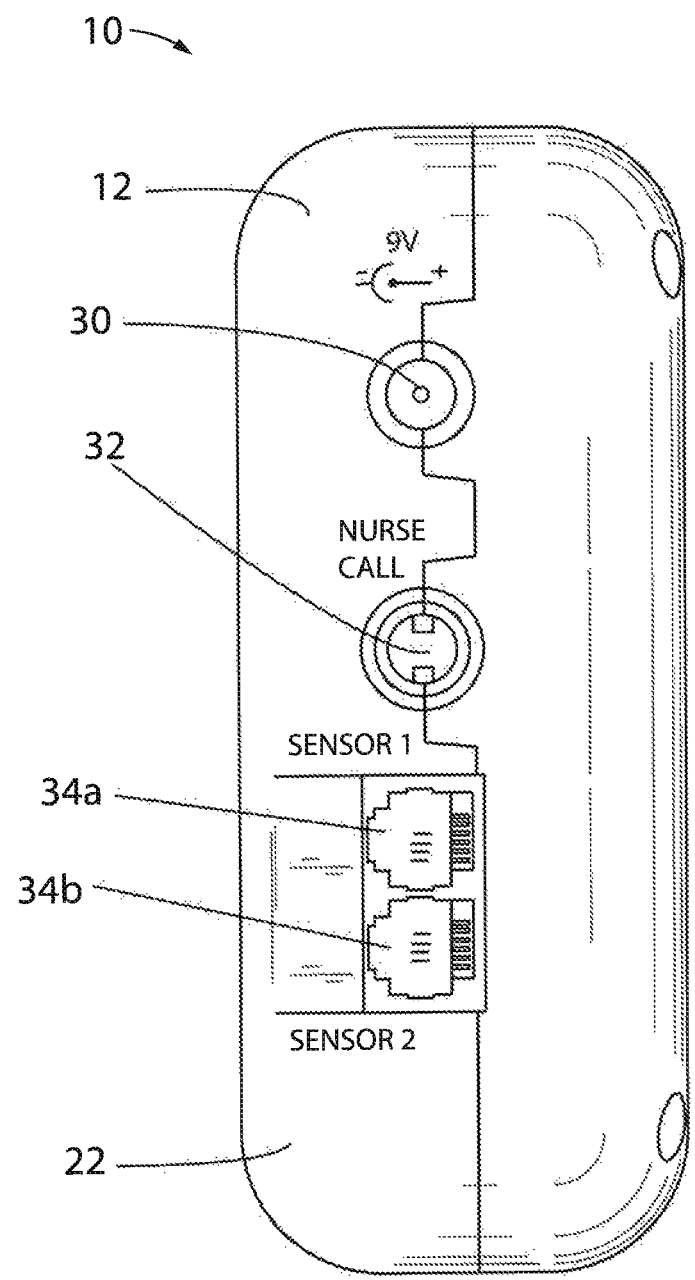
FIG. 3 is a first side view of the electronic fall monitoring system of FIG. 1.

As shown in the first side view of FIG. 3, the device 12 can include multiple wired and/or wireless connections or ports, including a power port 30 for connecting to a wired AC power source, a nurse call port 32 for connecting to a nurse's station (not shown), and multiple patient sensor ports 34, such as first and second sensor ports 34a and 34b, also identified as "Sensor 1" and "Sensor 2," respectively, for individually connecting to patient sensors. Each sensor port 34 can be operable to connect to a patient sensor for detecting an activation and/or deactivation of the patient sensor. An activation of a patient sensor could occur, for example, when a patient rests on the sensor indicating a physical presence at the sensor. A deactivation of a patient sensor could occur, for example, when a patient later moves from the sensor, indicating a loss of physical presence at the sensor. In addition to monitoring for such activations and/or deactivations, each sensor port 34 can also be monitored for connections and/or disconnections to sensors.

Figure 4:
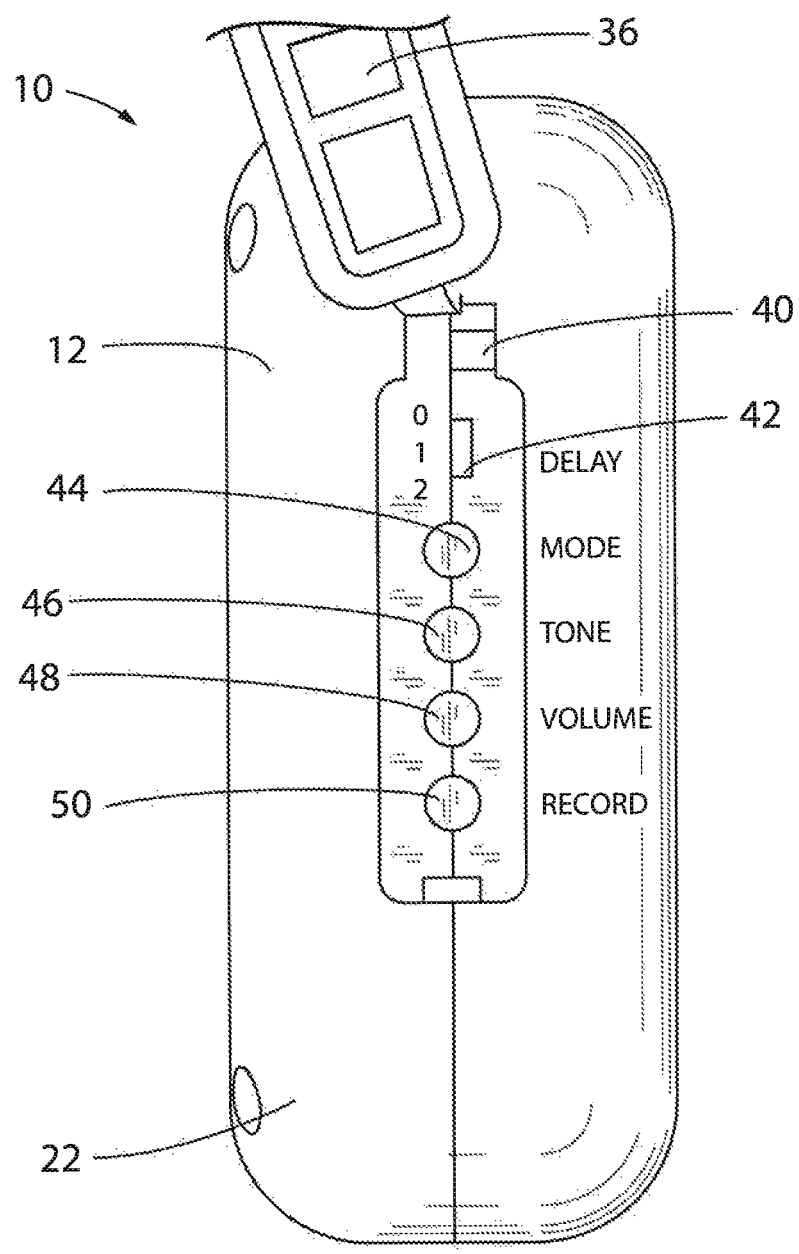
FIG. 4 is a second side view of the electronic fall monitoring system of FIG. 1.

As shown in the second side view of FIG. 4, the device 12 can include multiple configuration inputs for configuring the device 12. A housing cover 36 can cover or shield the configuration inputs when not in use. The configuration inputs can include, among other things: a sliding manual electric nurse call switch 40 for configuring the nurse call port 32 to operate normally open ("NO") or normally closed ("NC"); a sliding manual electric delay switch 42 for configuring a delay which must be met before a sensed deactivation at a patient sensor can cause an alarm, such as 0 (no delay), 1 second or 2 seconds; an alarm mode button 44 for configuring a type of alarm which occurs when a sensed deactivation at a patient sensor occurs, such as a playback of a recorded voice and an audible tone, playback of the recorded voice only, the audible tone only, or mute; a tone button 46 for configuring a different types of audible alarm tones, such as for distinguishing between different devices 12; a volume button 48 for configuring a volume of the alarm, such as low, medium or high; and/or a record button 50 for recording a voiced statement for playback during an alarm.

Figure 5:
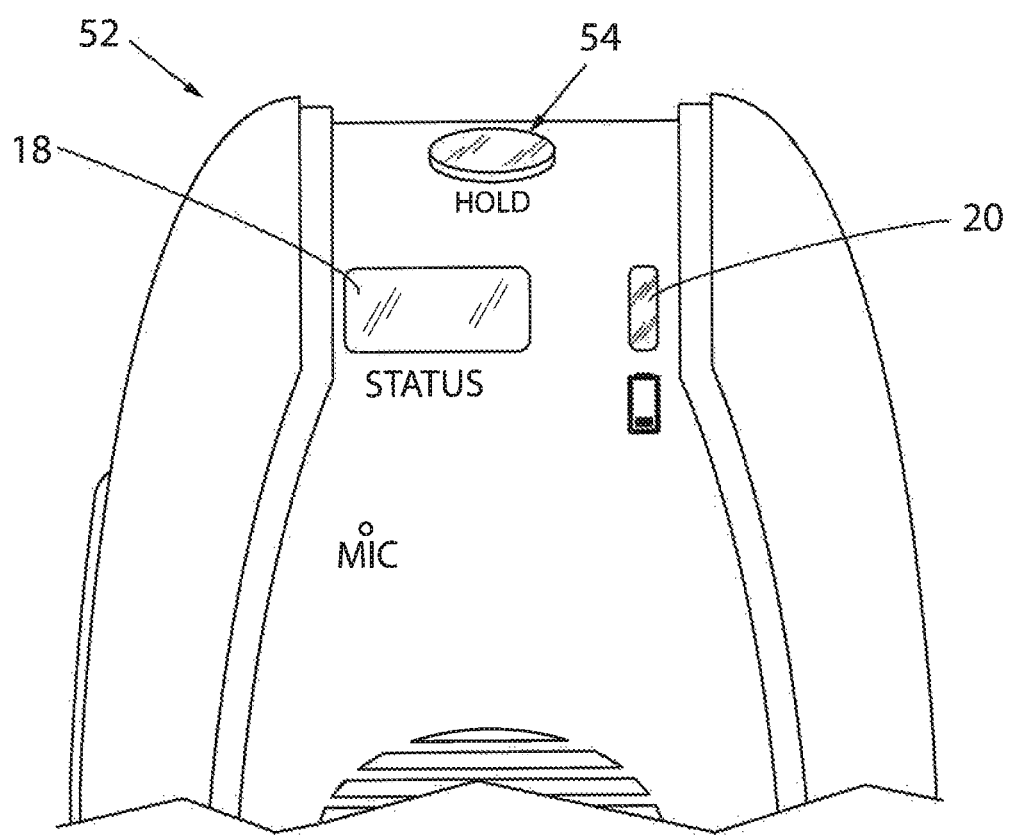
FIG. 5 is a detailed view illustrating a standby input and multi-color LED of the electronic fall monitoring system of FIG. 1.

As shown in FIG. 5, a detailed view 52 of the front of the device 12, a standby input 54 can be prominently positioned proximal to the LED 18. The standby input 54 can operate when pressed to temporary hold or suspend the device 12, from either the monitor mode or the alarm mode, to the standby mode. The standby input 54 can keep the device 12 in the standby mode for a predetermined amount of time, such as 30 seconds, each time the standby input 54 is pressed.

Referring now to FIGS. 6-14, in accordance with an aspect of the invention, a processor of the device 12 can execute a program stored in a non-transient medium of the device 12 for accomplishing various modes of operation (apart from any particular alarm mode), including the aforementioned standby, monitor and alarm modes. In addition, the processor can control the LED 18 to illuminate a color corresponding to a given mode, which color and mode can change based on various conditions encountered, such as yellow for standby, green for monitor and red for alarm. The numerated steps in each figure are correspondingly highlighted to indicate the particular mode of the step (see "Status Light Key" shown in FIG. 6).

Figure 6:
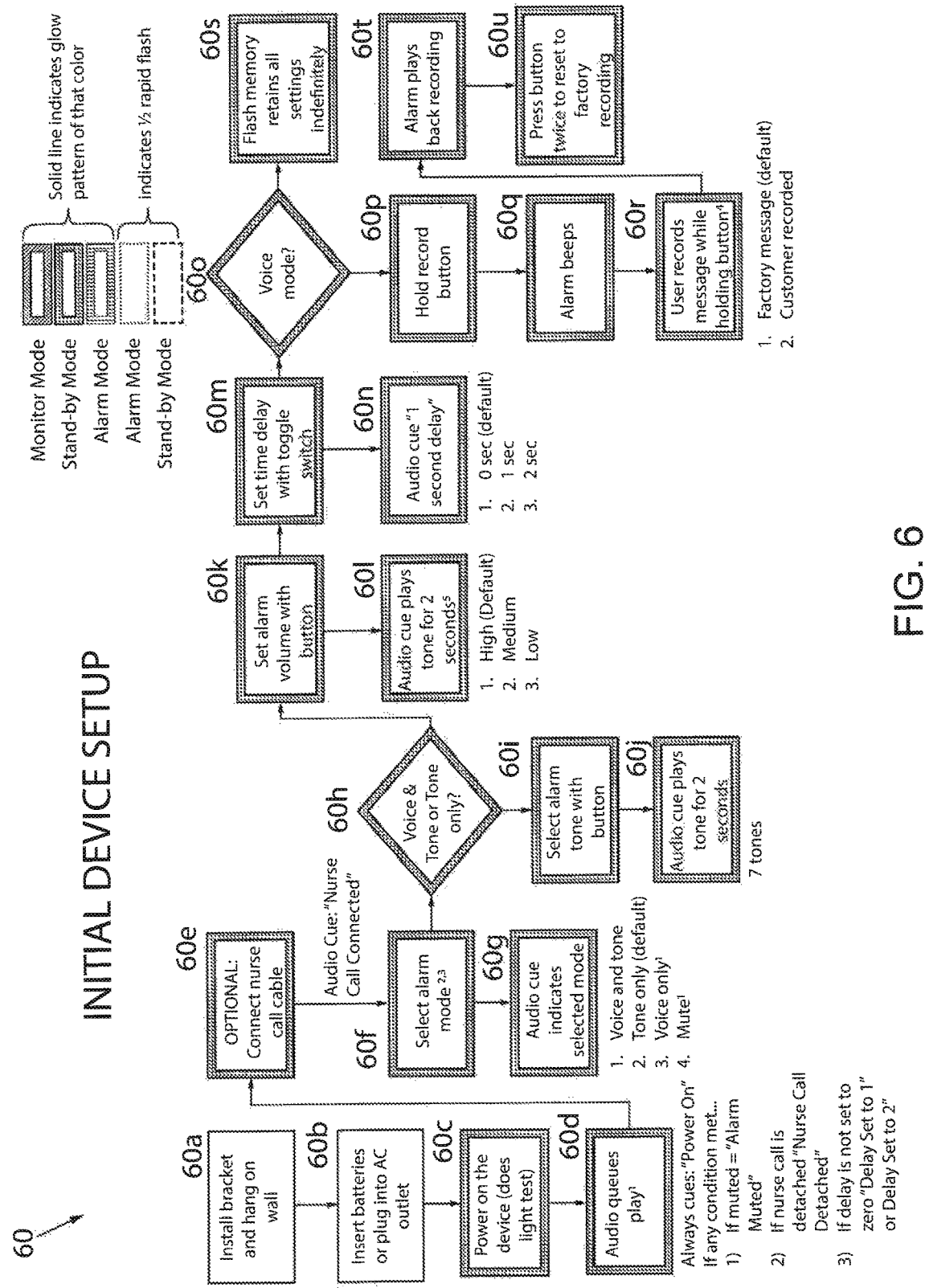
FIG. 6 is a flow chart illustrating initial set up with an electronic fall monitoring system in accordance with an aspect of the invention.

Referring to FIG. 6, a flow chart 60 illustrates an initial set up with the electronic fall monitoring system 10 in accordance with an aspect of the invention. At 60a, the device 12 can be installed in a support mechanism, such as a bracket, clip, bar or other arrangement, at the recess 23. At 60b-60c, batteries can be installed in the battery compartment, and/or AC power connected to the power port 30, turning on the device 12, bringing the device into the standby mode, and illuminating the LED 18 yellow. At 60d, an audio cue can play summarizing a current, default state to the user, such as "power on, alarm muted, nurse call disconnected, 1 second delay." At 60e, a nurse call cable can optionally be connected to the nurse call port 32 with the audio-cue "Nurse Call Connected." At 60f, the user can select a desired alarm mode via the alarm mode button 44 (apart from any particular mode of operation). At 60g, an audio cue can play summarizing the selected alarm mode, such as "voice and tone," or "tone only." Following 60h, when voice and tone is selected, or when tone only is selected, at 60i the user can select a desired alarm tone via the tone button 46, followed by an audio cue playing the specified tone at 60j. Also, following 60h, when voice and tone is selected, or when tone only is selected, at 60k the user can select a desired alarm volume via the volume button 48, followed by an audio cue playing the tone at the specified volume 60l. At 60m, the user can select a desired delay which must be met before the alarm can activate, such as 0 (no delay), 1 second or 2 seconds, via the delay switch 42, followed by an audio cue playing summarizing the delay at 60n. Following 60o, when voice is selected as the desired alarm mode, at 60p-60u, the user can record a statement through the microphone 14, which could be played back through the speaker 16 when the alarm is activated, using the record button 50. At 60s, a non-volatile memory retains each of the aforementioned user settings. The device 12 can be in the standby mode (with the LED 18 illuminated yellow) through each of the aforementioned steps. Although many configurations are discussed above, the user can skip certain configurations and accept default values where skipped. In addition, a reset function can be received to clear user selections and restore the system to default values.

Figure 7:
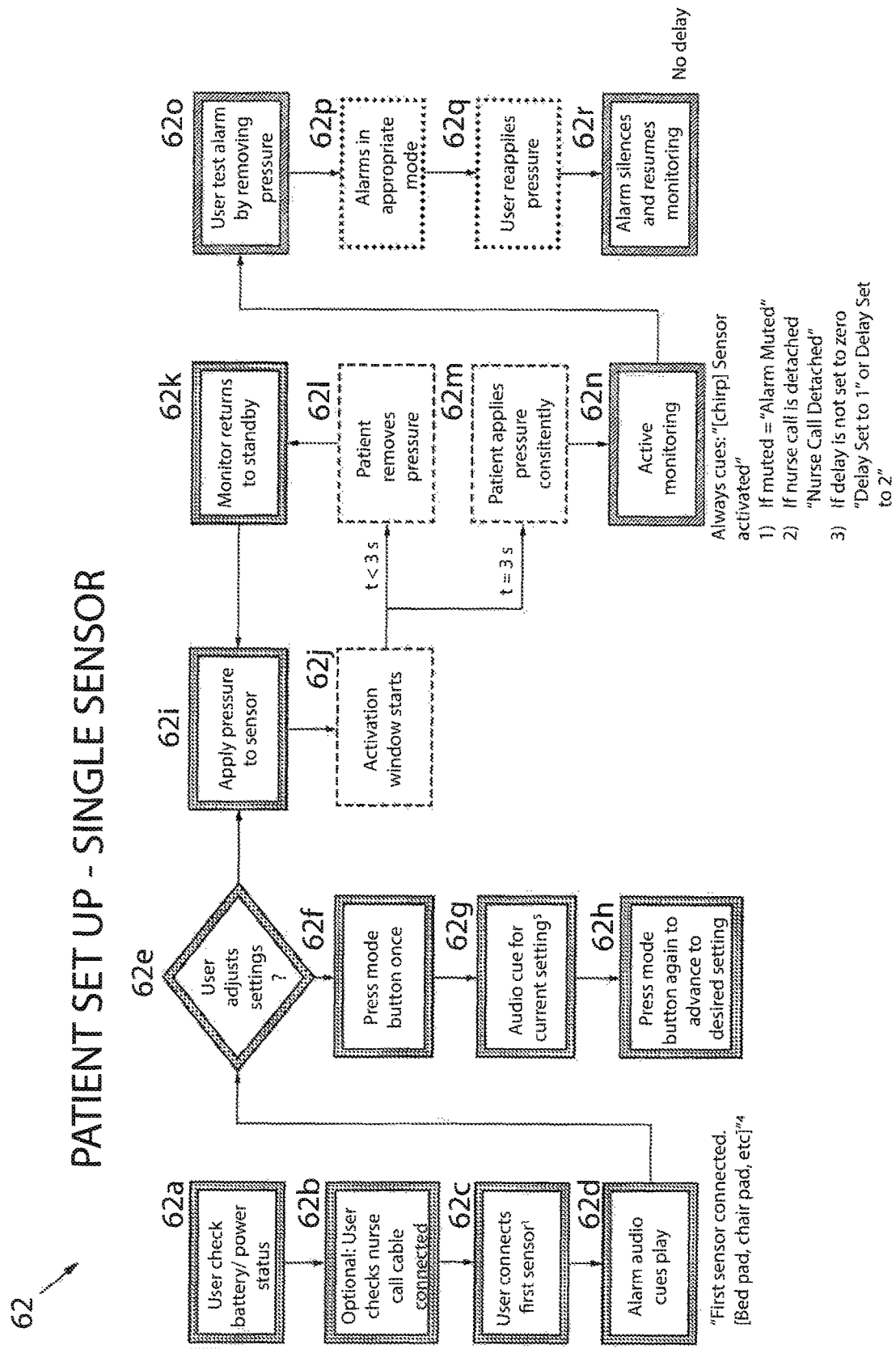
FIG. 7 is a flow chart illustrating single sensor set up with an electronic fall monitoring system in accordance with an aspect of the invention.

Referring to FIG. 7, a flow chart 62 illustrates a single patient sensor set up with the electronic fall monitoring system 10 in accordance with an aspect of the invention. In the standby mode, at 62a the user can check batter/power status, at 62b the user can check nurse cable connection status, at 62c the user can connect a first patient sensor to a first sensor port, such as first sensor port 34a, and at 62d an audio cue can play summarizing the sensor connection state, such as "first sensor connected." At 62e-62h, the user can configure the alarm settings to customize the alarm for the first patient sensor at the first sensor port. When additional patient sensors are connected, the user can similarly customize alarms for those sensors so as to distinguish alarms from among the sensors. The device 12 can be in the standby mode (with the LED 18 illuminated yellow) through each of the aforementioned steps. At 62i, the processor of device 12 can detect an activation of the sensor, upon an application of pressure or closing of a belt sensor on the sensor by the patient, indicating a physical presence at the sensor. At 62j, with the activation detected, the device 12 can transition to the monitor mode (with the LED 18 flashing yellow), and an audio cue can play summarizing the event and the current state, such as "sensor activation [beep], alarm muted, nurse call disconnected, 1 second delay." If at 62l a deactivation is detected within a predetermined amount of time, such as less than 3 seconds, the device 12 can return to the standby mode (the LED 18 illuminated yellow) at 62k, until another activation is detected at 62i. This provides hysteresis control. However, if at 62m the activation is maintained for at least the predetermined amount of time, such 3 seconds or more, the device 12 can continue in the monitor mode (with the LED 18 illuminated green) at 62n. Then, if at 62o the patient removes pressure from the sensor with a deactivation detected, the device 12 can transition to the alarm mode (with the LED 18 flashing red) at 62p, with the selected alarm being active, until pressure is reapplied to the sensor at 62q to silence the alarm and resume monitoring in the monitor mode (with the LED 18 illuminated green) at 62r.

Figure 8:
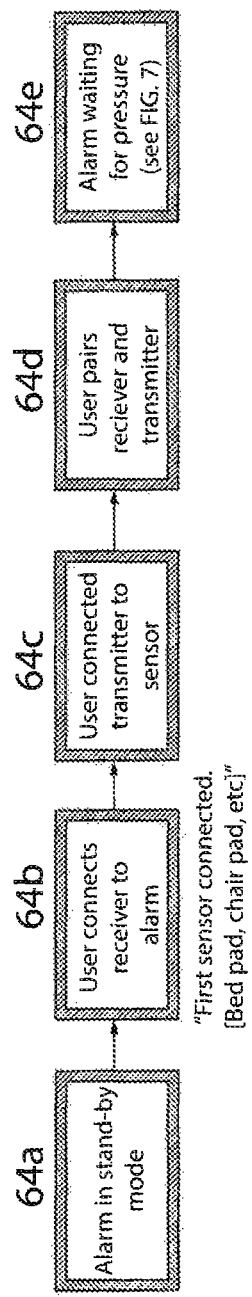
FIG. 8 is a flow chart illustrating wireless sensor set up with an electronic fall monitoring system in accordance with an aspect of the invention.

Referring to FIG. 8, a flow chart 64 illustrates a wireless sensor set up with the electronic fall monitoring system 10 in accordance with an aspect of the invention. While in the standby mode (the LED 18 illuminated yellow) at 64a-64e, a user can pair a wireless transmitter to wirelessly transmit the activation/deactivation events to a wireless receiver connected to a sensor port 34 of the device 12. Then, similar to the flow chart 62, the processor of device 12 can wirelessly detect an activation of the sensor, upon an application of pressure on the sensor by the patient, indicating a physical presence at the sensor, with active monitoring and hysteresis control.

Figure 9:
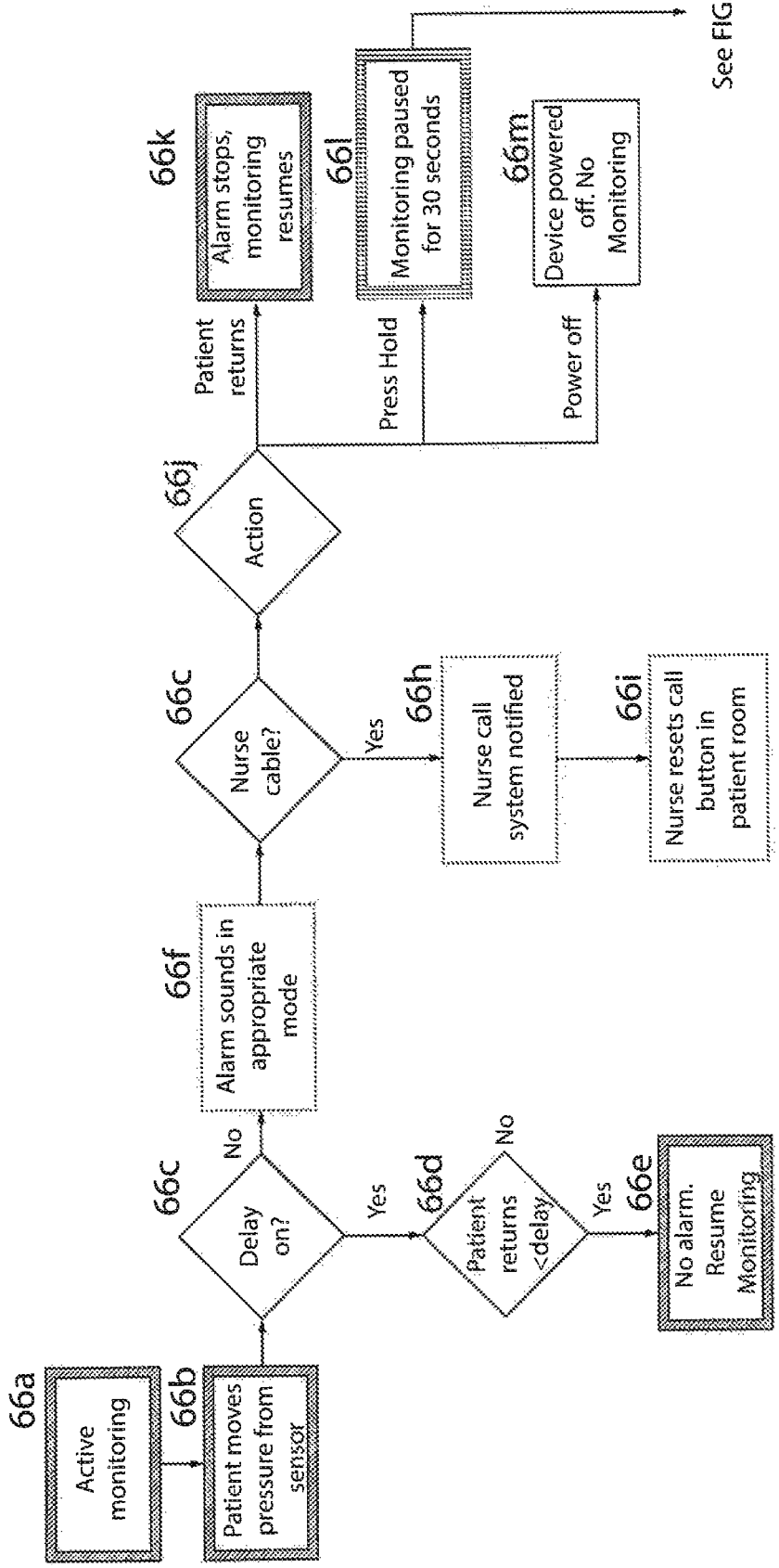
FIG. 9 is a flow chart illustrating single sensor monitoring with an electronic fall monitoring system in accordance with an aspect of the invention.

Referring to FIG. 9, a flow chart 66 illustrates monitoring in with the electronic fall monitoring system 10 with a single sensor, by way of example, in accordance with an aspect of the invention. While in the monitor mode (with the LED 18 illuminated green) at 66a, a deactivation is detected at 66b, the processor can determine with a delay has been set, via the delay switch 42, at 66c. If a delay has been set (Yes), at 66d, the processor can determine whether a re-activation is detected (the patient promptly returns to the sensor) within the time period allowed by the delay. If the re-activation is detected, with the patient returning to the sensor within the time period allowed by the delay (Yes), the device 12 does not enter the alarm mode, but rather continues in the monitor mode (with the LED 18 illuminated green). However, if at 66c a delay was not set (No), or if at 66d the re-activation does not occur, with the patient failing to return to the sensor within the time period allowed by the delay (No), at 66f the device 12 can transition to the alarm mode (with the LED 18 flashing red). At 66g, if a nurse cable is connected, the nurse call station will be notified for action at 66h-66i (with the LED 18 flashing red). At 66j, the processor can analyze several actions for proceeding. At 66k, if a re-activation is detected, with the patient returning to the sensor, the device 12 can transition back to the monitor mode (with the LED 18 illuminated green). Alternatively, if at 66j the standby input 54 is pressed, the device 12 can transition to the standby mode (the LED 18 illuminated red) at 66l, and with additional reference to FIG. 10A, when a re-activation is detected, with the patient returning to the sensor, the device 12 can transition back to the monitor mode (with the LED 18 illuminated green) at 68a. If at 66m the device is powered off, such as by turning the power switch 24 off, the device 12 will be turned off completely with no monitoring or illumination of the LED 18.

Figure 10A:
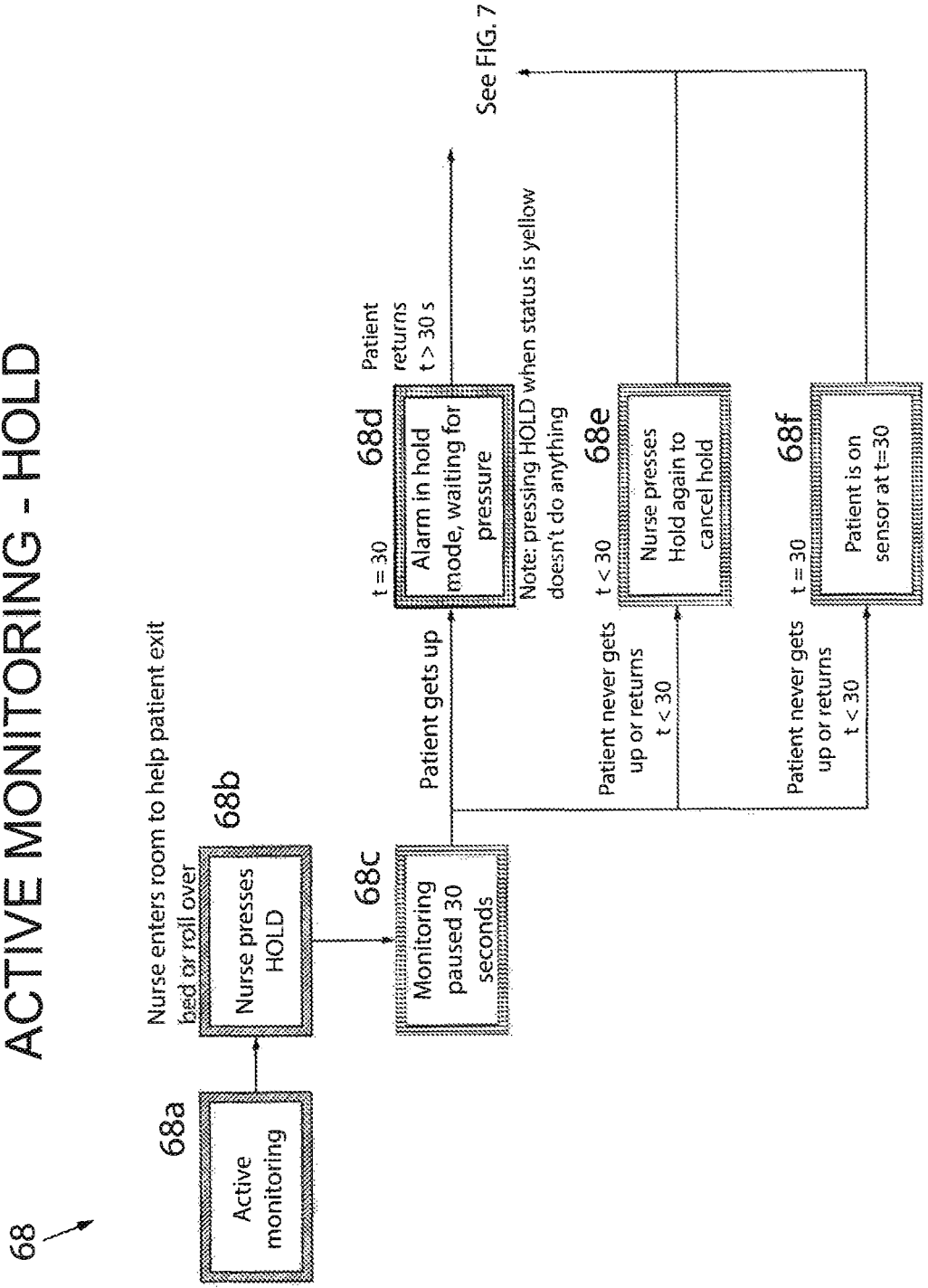
FIG. 10A is a flow chart illustrating single sensor monitoring and hold with an electronic fall monitoring system in accordance with an aspect of the invention.

Referring to FIG. 10A, a flow chart 68 illustrates single sensor monitoring and hold with the electronic fall monitoring system 10 in accordance with an aspect of the invention. While in the monitor mode (with the LED 18 illuminated green) at 68a, a user can press the standby input 54 at 68b for a first duration, such as less than 3 seconds, to transition to the alert mode (the LED 18 illuminated red) at 68c for a predetermined amount of time, such as 30 seconds or less. In one aspect, while in the alert mode, the processor can analyze several actions for proceeding. At 68d, if a deactivation is detected within the predetermined amount of time, such as less than the 30 seconds, the LED 18 can illuminate yellow, and the device 12 can move to the standby mode until returning to the monitor mode (see FIG. 7). Also, at 68e, if a deactivation is not detected within the predetermined amount of time, with the LED 18 remaining red, the user can press the standby input 54 again, to clear the delay as needed, returning to the monitor mode (see FIG. 7). Regardless, at 68f, if an activation (or re-activation) is detected when the predetermined amount of time expires, such as at the 30 seconds, the device 12 can return to the monitor mode (see FIG. 7). Then, according to the flow chart 62, the processor of device 12 can continue with active monitoring and hysteresis control.

Figure 10B:
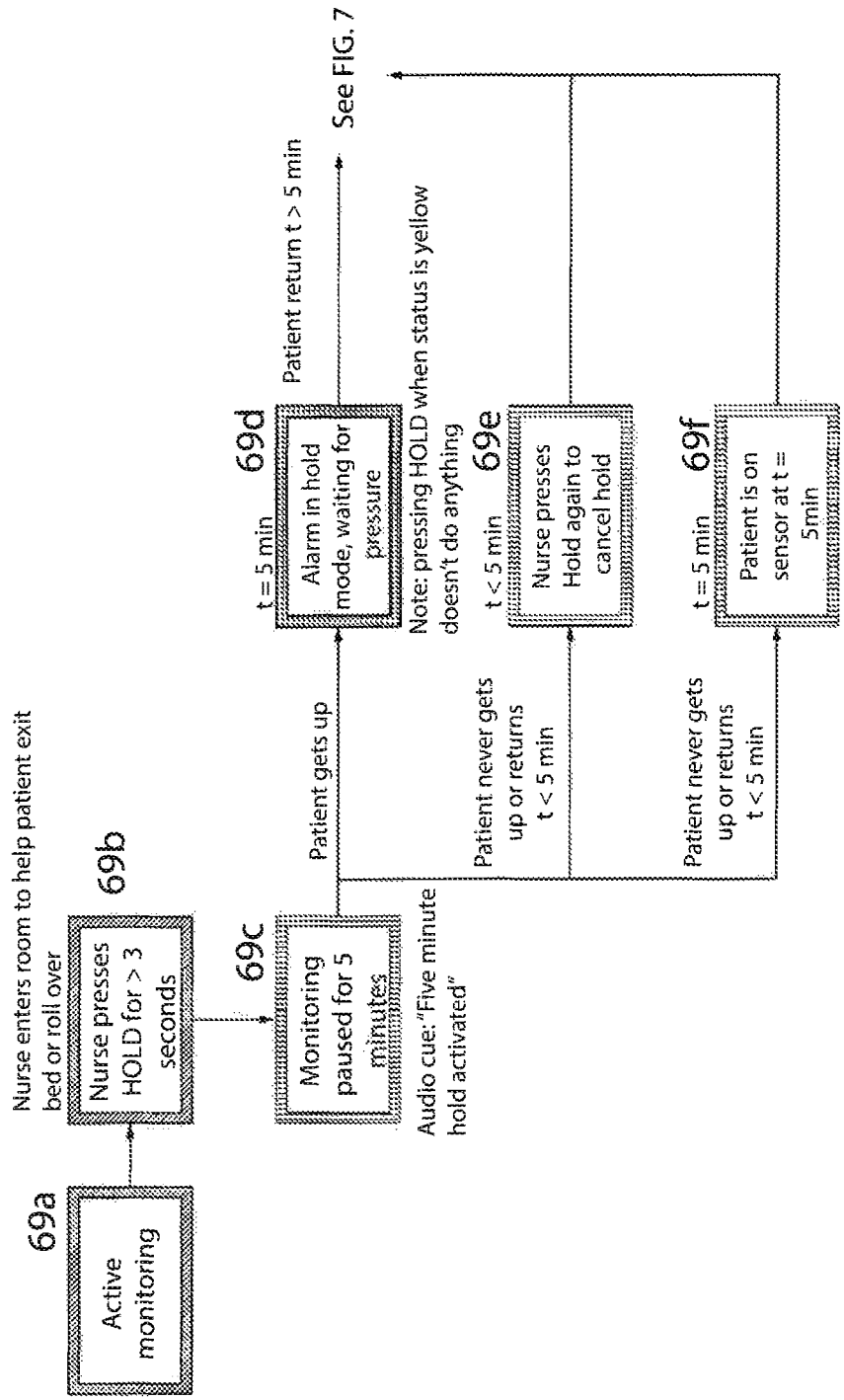
FIG. 10B is a flow chart illustrating single sensor monitoring and extended hold with an electronic fall monitoring system in accordance with an aspect of the invention.

Referring to FIG. 10B, a flow chart 69 illustrates single sensor monitoring and extended hold with the electronic fall monitoring system 10 in accordance with an aspect of the invention. While in the monitor mode (with the LED 18 illuminated green) at 69a, a user can press the standby input 54 at 69b for a second duration, such as more than 3 seconds, to transition to the alert mode (the LED 18 illuminated red) at 69c for an extended predetermined amount of time, such as 5 minutes or more. In one aspect, while in the alert mode, the processor can analyze several actions for proceeding. At 69d, and referring again to FIG. 7, if a deactivation is detected within the extended predetermined amount of time, such as less than the 5 minutes, the LED 18 can illuminate yellow, and the device 12 can move to the standby mode until returning to the monitor mode (see FIG. 7). Also, at 69e, if a deactivation is not detected within the extended predetermined amount of time, with the LED 18 remaining red, the user can press the standby input 54 again, to clear the delay as needed, returning to the monitor mode at (see FIG. 7). Regardless, at 69f, if an activation (or re-activation) is detected when the extended predetermined amount of time expires, such as at the 5 minutes, the device 12 can return to the monitor mode at (see FIG. 7). Then, according to the flow chart 62, the processor of device 12 can continue with active monitoring and hysteresis control.

Figure 11:
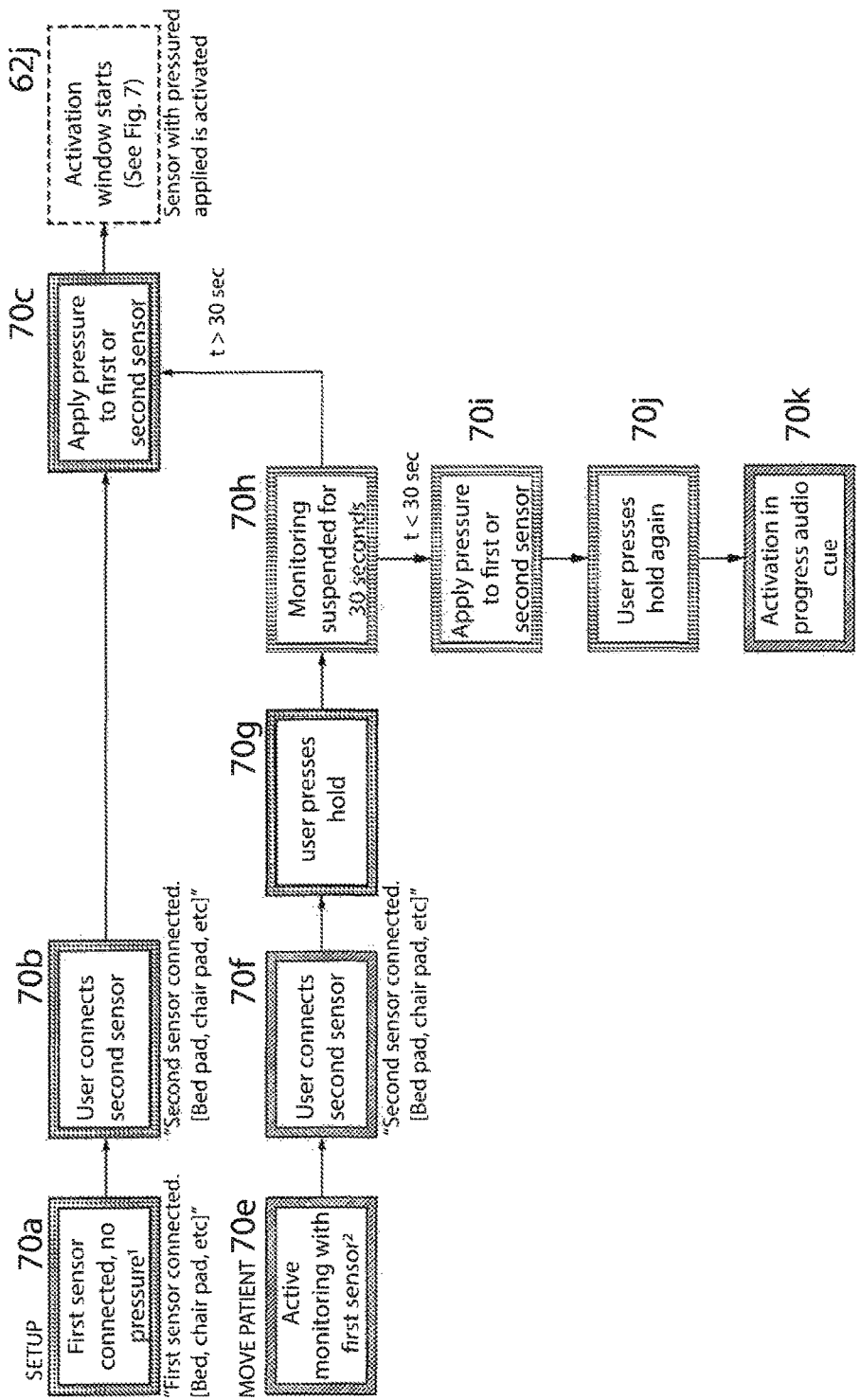
FIG. 11 is a flow chart illustrating multi sensor set up with an electronic fall monitoring system in accordance with an aspect of the invention.

Referring to FIG. 11, a flow chart 70 illustrates a multi sensor set up with the electronic fall monitoring system 10 in accordance with an aspect of the invention. At 70a, in the standby mode, a user can connect a first patient sensor (such as to the first sensor port 34a) with a first corresponding audio cue being played, and at 70b the user can connect a second patient sensor (such as to the second sensor port 34b) with a second corresponding audio cue being played. At 70c, the processor of device 12 can detect an activation of a sensor, either the first sensor or the second sensor, and correspondingly transition to 62j (with the LED 18 flashing yellow) (see FIG. 7), monitoring such first or second sensor. In other words, multiple sensors can be connected while in the standby mode, but not until one of the sensors is activated will the device 12 enter the monitor mode. In another path, at 70e the device 12 may already be in the monitor mode (with the LED 18 illuminated green), actively monitoring the first patient sensor (which may be connected to the first sensor port 34a). Then, at 70f, a user can freely connect a second patient sensor (such as to the second sensor port 34b) with a second corresponding audio cue being played, still in the monitor mode. To adjust the patient from one sensor to the other, at 70g a user can press the standby input 54 (the LED 18 illuminated yellow), which can transition the device 12 to the alert mode (the LED 18 illuminated red) at 70h for the predetermined amount of time, such as 30 seconds. Still in the alert mode, at 70i, the patient can apply pressure to either the first or second sensor, and at 70j the user can press the standby input 54 again, to clear the delay as needed. At 70k, temporary transition to the alert mode can then expire, returning to the monitor mode (with the LED 18 illuminated green). At 70c and 62j, monitoring resumes for the sensor on which pressure was applied at 70i. In other words, using the standby input 54, a patient can be transitioned from one sensor to the next.

Figure 12:
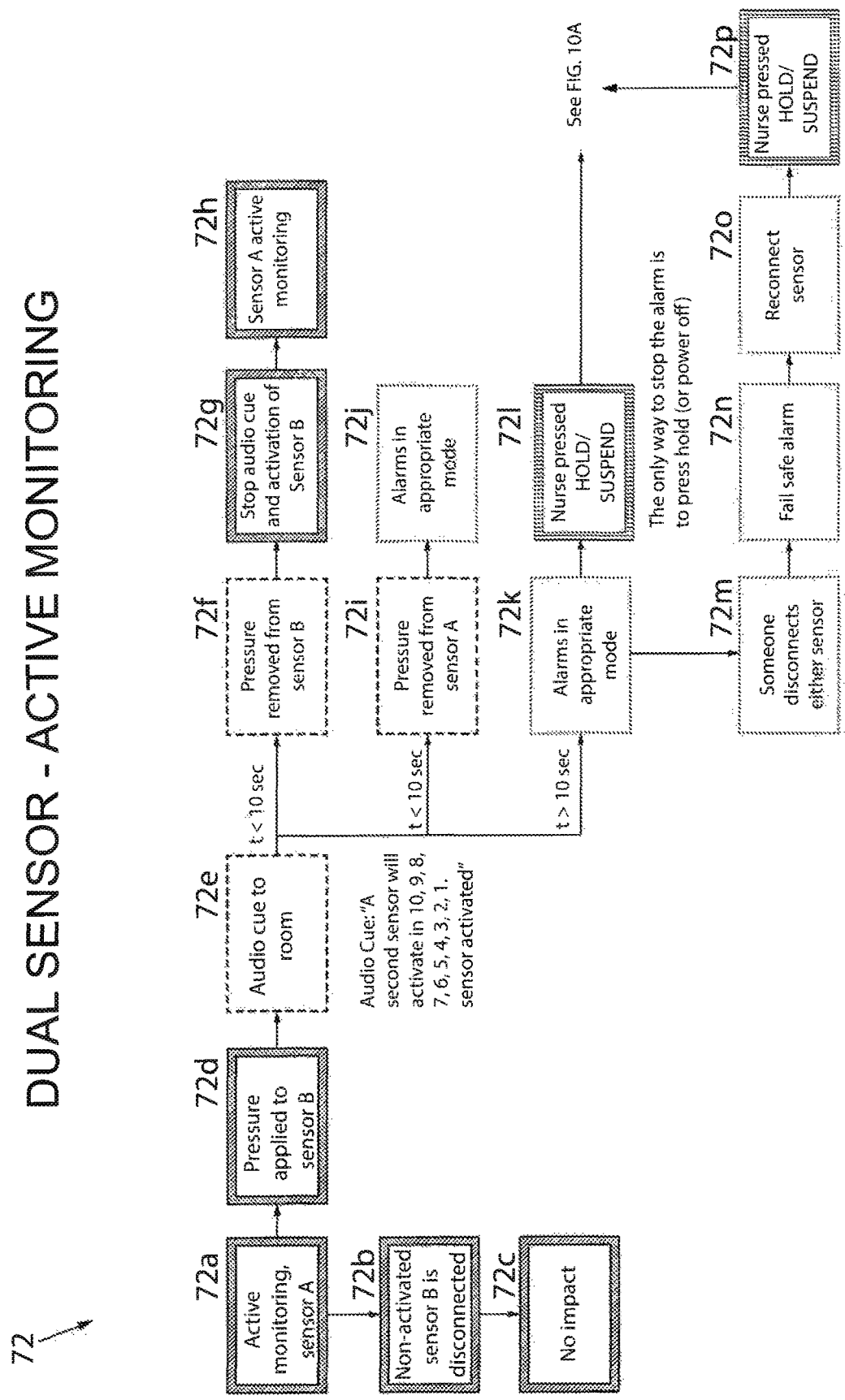
FIG. 12 is a flow chart illustrating multi sensor monitoring with an electronic fall monitoring system in accordance with an aspect of the invention.

Referring to FIG. 12, a flow chart 72 illustrates multi sensor monitoring with the electronic fall monitoring system 10 in accordance with an aspect of the invention. At 72a, a first patient sensor (which may be connected to the first sensor port 34a) (also "sensor A" or "primary sensor") can be monitored by the device 12 in the monitor mode (with the LED 18 illuminated green) while a second patient sensor (which may be connected to the first sensor port 34b) (also "sensor B" or "secondary sensor") is also connected. At 72b, the second patient sensor can be disconnected. However, despite such disconnection, the device 12 continues monitoring the primary patient sensor at 72c in the monitor mode without any impact. At 72d, the processor can detect an activation of the second patient sensor. At 72e, the device can transition to the standby mode (with the LED 18 flashing yellow) and an audio cue can play a warning with a countdown corresponding to a predetermined amount of time, such as "A second sensor will activate in 10, 9, 8, 7, 6, 5, 4, 3, 2, 1." In one aspect, a signal can also be sent to the nurse call station at 72e. At 72f, upon detecting a deactivation at the second patient sensor within the predetermined amount of time, the device 12 can simply transition back to the monitor mode (with the LED 18 illuminated green) and cease playing the warning at 72g, while continuing to monitor the first patient sensor in the monitor mode at 72h. In other words, multiple sensors can be connected while in the monitor mode, but only one sensor will be monitored, the one sensor being the sensor originally causing entry into the monitor mode. Alternatively, at 72i upon detecting a deactivation at the first patient sensor within the predetermined amount of time, the device 12 can transition to the alert mode (with the LED 18 flashing red) at 72j until resolved. Alternatively, at 72k upon expiration of the predetermined amount of time without any action, the device 12 can transition to the alert mode (with the LED 18 flashing red) at 72k. This can continue until the standby input 54 is pressed to stop the alarm at 72l, with the device 12 transitioning back to the monitor mode (with the LED 18 illuminated green) at 68*a*. However, if at 72*k* either the primary or secondary patient sensor is disconnected, the device 12 can transition to a fail-safe alarm at 72*n*. This can continue until the disconnected sensor(s) is/are reconnected. The alarm mode can continue until the standby input 54 is pressed to stop the alarm at 72*p*, with the device 12 transitioning back to the monitor mode (with the LED 18 illuminated green) at 68*a*

Figure 13:
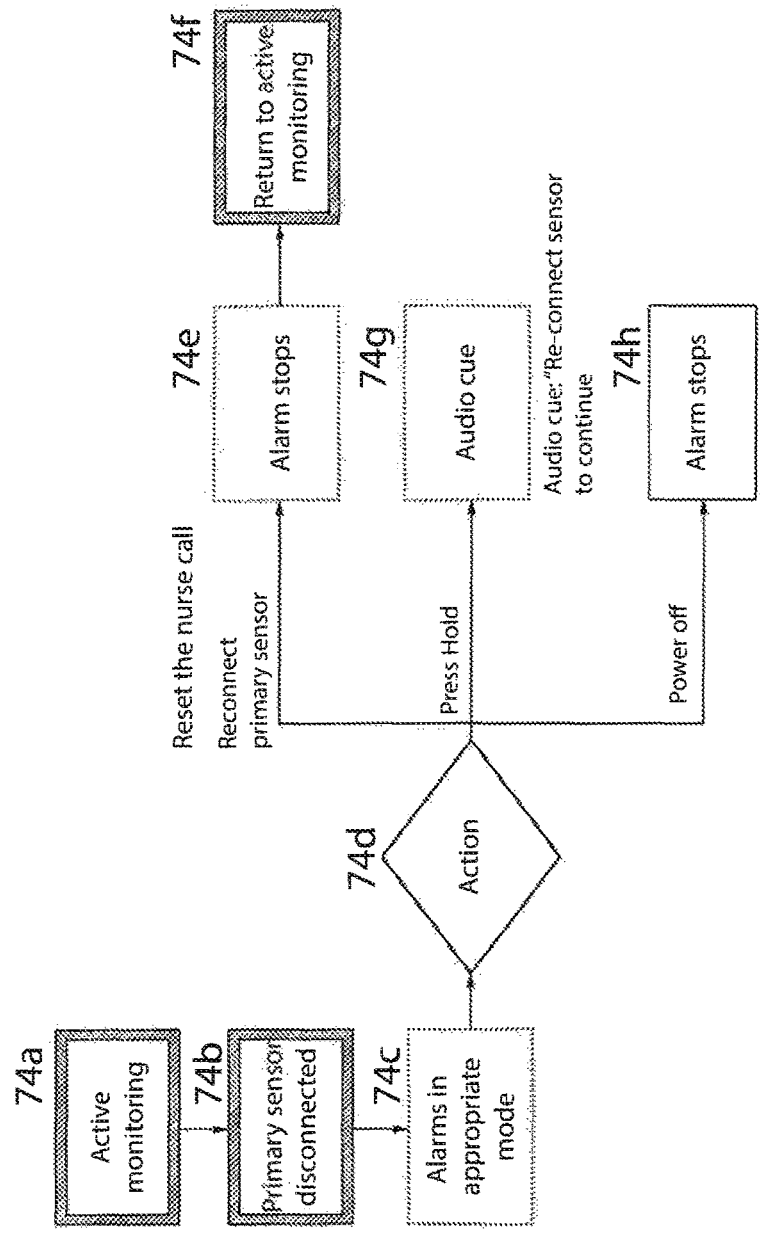
FIG. 13 is a flow chart illustrating sensor error modes with an electronic fall monitoring system in accordance with an aspect of the invention.

Referring to FIG. 13, a flow chart 74 illustrates sensor error modes with the electronic fall monitoring system 10 in accordance with an aspect of the invention. At 74*a*, while actively monitoring a first patient sensor (which may be connected to the first sensor port 34*a*) (also "sensor A" or "primary sensor") in the monitor mode (with the LED 18 illuminated green), a disconnection of the first patient sensor at 74*b* can cause a transition to the alarm mode (the LED 18 flashing red) at 74*c*. In such an instance, at 74*d*, the processor can analyze several actions for proceeding. At 74*e*, a re-connection of the first sensor can transition back to the monitor mode (with the LED 18 illuminated green) at 74*f*. Alternatively, if at 74*g* the standby input 54 is pressed, the device 12 can play an audio cue while in the alarm mode, such as "re-connect sensor to continue." Alternatively, if at 74*h* the device is powered off, such as by turning the power switch 24 off, the device 12 will be turned off completely with no monitoring or illumination of the LED 18.

Figure 14:
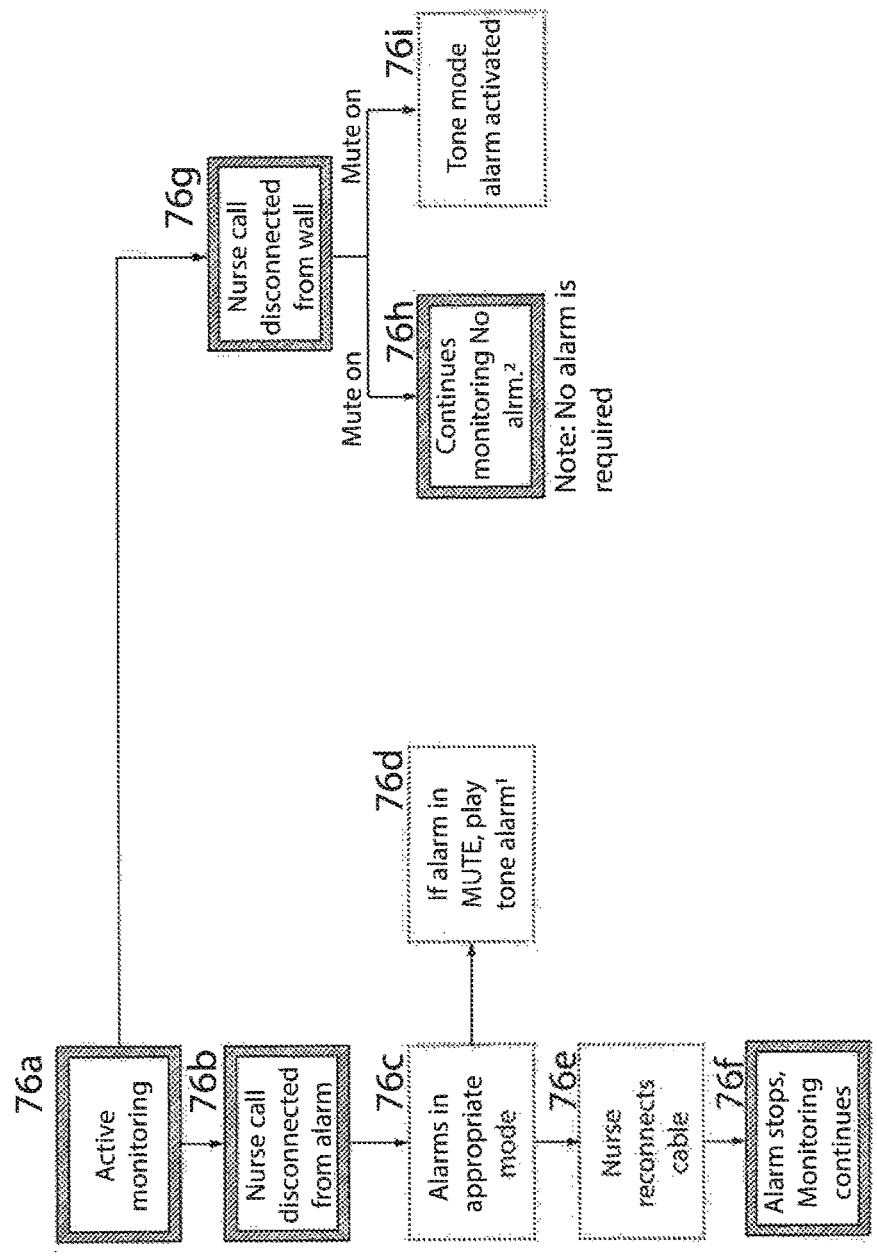
FIG. 14 is a flow chart illustrating nurse call error modes with an electronic fall monitoring system in accordance with an aspect of the invention.

Referring to FIG. 14, a flow chart 76 illustrates nurse call error modes with the electronic fall monitoring system 10 in accordance with an aspect of the invention. At 76*a*, while actively monitoring a patient sensor in the monitor mode (with the LED 18 illuminated green), the processor of the device 12 can detect a disconnection of the nurse call port 32 from the device itself at 76*b*. This can cause a transition to the alarm mode (the LED 18 flashing red) at 76*c*. If the alarm is in mute, the device 12 can play a tone alarm at 76*d*. The alarm mode will continue until the nurse call port 32 is re-connected at 76*e*, at which point the device 12 will return to the monitor mode (with the LED 18 illuminated green) at 76*f*. However, while actively monitoring the patient sensor in the monitor mode (with the LED 18 illuminated green) at 76*a*, if the processor of the device 12 instead detects a disconnection of the nurse call port 32 from the wall at 76*g* (with a cable still attached to the device itself at the nurse call port 32), the processor can determine whether the alarm is muted. If the alarm is not muted ("mute off"), the device 12 can continue to monitor the patient sensor in the monitor mode (with the LED 18 illuminated green) at 76*h*. However, if the alarm is muted ("mute on"), the device 12 can transition to the alarm mode (the LED 18 flashing red) at 76*i*. In addition, or alternatively, at 76*i*, if the alarm is muted ("mute on"), the device 12 can play an audio cue warning indicating "nurse call detached," and/or can cease muting ("mute off").

Many different audio cues can advantageously be played to correspond with various states and modes of the system as described above, including with respect to steps of FIGS. 6-14. Audio cues can include, for example: "ALARM RESET," "POWER ON," "BEGIN RECORD," "END RECORD," "VOLUME LOW," "VOLUME MEDIUM," "VOLUME HIGH," "TONE MODE," "VOICE MODE," "VOICE AND TONE MODE," "MUTE MODE," "SENSOR ONE ATTACHED," "SENSOR TWO ATTACHED," "SENSOR ONE ACTIVATED," "SENSOR TWO ACTIVATED," "SENSOR DETACHED," "TWO SENSORS IN USE," "PLEASE DON'T GET UP, SIT BACK DOWN AND USE THE CALL," "BUTTON TO CALL FOR HELP," "ZERO DELAY," "ONE SECOND DELAY," "TWO SECOND DELAY," "NURSE CALL ATTACHED," "NURSE CALL DETACHED," "LOW BATTERY," "FAILED SELF TEST," "AC ADAPTER CONNECTED," "AC ADAPTER DISCONNECTED," "PATIENT MONITORING RESUMED," "YOU HAVE ACTIVATED A SECOND SENSOR, PLEASE REMOVE PRESSURE WITHIN 10 SECONDS," and/or "ALARM SUSPEND." A default alarm message could comprise the following audio cue: "PLEASE DON'T GET UP. SIT BACK DOWN AND USE THE CALL BUTTON TO CALL FOR HELP." Such audio cues can be correspondingly played in the steps above as appropriate to give user guidance.

Certain terminology is used herein for purposes of reference only, and thus is not intended to be limiting. For example, terms such as "upper," "lower," "above," and "below" refer to directions in the drawings to which reference is made. Terms such as "front," "back," "rear," "bottom," "side," "left" and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second" and other such numerical terms referring to structures do not imply a sequence or order unless clearly indicated by the context.

When introducing elements or features of the present disclosure and the exemplary embodiments, the articles "a," "an," "the" and "said" are intended to mean that there are one or more of such elements or features. The terms "comprising," "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as coming within the scope of the following claims. All of the publications described herein including patents and non-patent publications are hereby incorporated herein by reference in their entireties.

What is claimed is:

1. An electronic fall monitoring system, comprising:
a plurality of sensor ports, each sensor port being operable to connect to a patient sensor for detecting an activation indicating a physical presence at the patient sensor and a deactivation indicating a loss of physical presence at the patient sensor;
a standby input; and
a processor executing a program stored in a non-transient medium, the processor executing the program to:
select a mode from among a plurality of modes, the plurality of modes including a monitor mode in which a sensor port connected to the patient sensor is monitored for the deactivation, an alarm mode in which an alarm is active following the deactivation detected in the monitor mode, and a standby mode in which the alarm is inactive, wherein the standby mode is selected before an activation is detected at any sensor port, wherein the monitor mode is selected when the activation is detected at a first sensor port, wherein the alarm mode is selected when the deactivation is detected at the first sensor port following the activation, and wherein selection of the standby input causes a temporary transition to the standby mode from either the monitor mode or the alarm mode.

2. The system of claim 1, wherein the activation detected at a second sensor port when in the monitor mode causes an audio cue to indicate activation of a second patient monitor when one patient monitor is already active.

3. The system of claim 1, wherein the monitor mode is selected when the deactivation is detected at a second sensor port which follows the activation at the second sensor port.

4. The system of claim 1, further comprising a multi-color Light Emitting Diode (LED), wherein the processor executes to illuminate the multi-color LED in a given color for indicating a given mode of the plurality of modes.

5. The system of claim 4, wherein the plurality of colors include green indicating the monitor mode, red indicating the alarm mode and yellow indicating the standby mode.

6. The system of claim 1, wherein selection of the standby input during the alarm mode causes an audio cue to be played for resolving the alarm mode.

7. The system of claim 1, further comprising a nurse call port, wherein the alarm mode is selected when a disconnection is detected at the nurse call port.

8. The system of claim 1, wherein selection of the standby input for a first duration causes a transition to the standby mode for a first predetermined amount of time, and wherein selection of the standby input for a second duration causes a transition to the standby mode for a second predetermined amount of time.

9. The system of claim 1, wherein the first predetermined amount of time is 30 seconds or less, and wherein the second predetermined amount of time is 5 minutes or more.

10. An electronic fall monitoring system, comprising:
a plurality of sensor ports, each sensor port being operable to connect to a patient sensor for detecting an activation indicating a physical presence at the patient sensor and a deactivation indicating a loss of physical presence at the patient sensor;
a multi-color Light Emitting Diode (LED); and
a processor executing a program stored in a non-transient medium, the processor executing the program to:
select a mode from among a plurality of modes, the plurality of modes including a monitor mode in which a sensor port connected to the patient sensor is monitored for a deactivation, an alarm mode in which an alarm is active following the deactivation, and a standby mode in which the alarm is inactive, and
illuminate the multi-color LED in a given color for indicating a given mode of the plurality of modes.

11. The system of claim 10, wherein the plurality of colors include green indicating the monitor mode, red indicating the alarm mode and yellow indicating the standby mode.

12. The system of claim 11, wherein the processor executes to selectively flash the multi-color LED in the monitor and alarm modes.

13. The system of claim 10, further comprising a speaker, wherein the processor further executes to play audio cues providing operating instructions in each of the plurality of modes.

14. The system of claim 13, wherein an audio cue in the standby mode indicates a patient monitor is connected to the sensor port.

15. The system of claim 13, wherein an audio cue in the monitor mode indicates the activation of a second patient monitor when one patient monitor is already active.

16. The system of claim 13, wherein an audio cue in the alarm mode indicates to reconnect a disconnected patient sensor.

17. An electronic fall monitoring system, comprising:
a housing enclosing a plurality of electronics including a processor;
a plurality of sensor ports accessible through the housing, each sensor port being operable to connect to a patient sensor for allowing the processor to detect an activation indicating a physical presence at the patient sensor and a deactivation indicating a loss of physical presence at the patient sensor;
a power switch accessible through the housing for controlling power to the plurality of electronics; and
a recess in the housing shaped for mounting the housing to a support mechanism, wherein the power switch is disposed in the recess so that the power switch is inaccessible when the housing is mounted to the support mechanism.

18. The system of claim 17, wherein the power switch is configured to allow actuation by hand without requiring a tool.

19. The system of claim 17, wherein the recess is provided on a back of the housing.

20. The system of claim 19, further comprising a multi-color LED provided on a front of the housing, wherein the multi-color LED is configured to illuminate in a plurality of colors for indicating a plurality of modes.

* * * * *